(12) United States Patent
Bartley et al.

(10) Patent No.: US 8,501,753 B2
(45) Date of Patent: Aug. 6, 2013

(54) USEFUL PHARMACEUTICAL SALTS OF 7-[(3R, 4R)-3-HYDROXY-4-HYDROXYMETHYL- PYRROLIDIN- 1-YLMETHYL]-3, 5-DIHYDRO-PYRROLO [3, 2-D] PYRIMIDIN-4-ONE

(75) Inventors: Gary Bartley, Boiling Springs, SC (US); Thomas Cleary, Pleasanton, CA (US); John Lang, Florence, SC (US)

(73) Assignee: BioCryst Pharmaceuticals, Inc., Durham, NC (US)

( * ) Notice: Subject to any disclaimer, the term of this patent is extended or adjusted under 35 U.S.C. 154(b) by 0 days.

(21) Appl. No.: 13/258,497

(22) PCT Filed: Mar. 24, 2010

(86) PCT No.: PCT/US2010/028490
§ 371 (c)(1),
(2), (4) Date: Mar. 16, 2012

(87) PCT Pub. No.: WO2010/111381
PCT Pub. Date: Sep. 30, 2010

(65) Prior Publication Data
US 2012/0165526 A1    Jun. 28, 2012

Related U.S. Application Data

(60) Provisional application No. 61/162,805, filed on Mar. 24, 2009.

(51) Int. Cl.
*C07D 487/04* (2006.01)
*A61K 31/513* (2006.01)

(52) U.S. Cl.
USPC ........................ 514/265.1; 544/280

(58) Field of Classification Search
USPC ...................... 544/280; 514/265.1
See application file for complete search history.

(56) References Cited

FOREIGN PATENT DOCUMENTS
WO    WO2004018496    *   3/2004
WO    WO2004/018496 A1 *  3/2007

OTHER PUBLICATIONS

Berge, 1977, Journal of Pharmaceutical Sciences, vol. 66, No. 1, p. 1-19.*
Mahmoud Ghanem, et. al., "Altered thermodynamics from remote mutations altering human toward bovine purine nucleoside phosphorylase," *Biochemistry* (2008) 47: 2559-2564.
Agnes Rinaldo-Matthis, el. al., "L-Enantiomers of transition state analogue inhibitors bound to human purine nucleoside phosphorylase," *Journal of the American Chemical Society* (2008), 130(3): 842-844.
Pravin L. Kotian, et. al., "A practical large-scale synthesis of (3r,4r)-4-(hydroxymethyl)pyrrolidin-3-ol via asymmetric 1,3-dipolar cycloaddition", *Organic Process Research & Development* (2005) 9(2):193-197.

* cited by examiner

*Primary Examiner* — Wu-Cheng Winston Shen
*Assistant Examiner* — Karen Cheng
(74) *Attorney, Agent, or Firm* — Bradley Arant Boult Cummings, LLP

(57) ABSTRACT

The present disclosure provides novel hemi- and mono-salts of 7-[(3R,4R)-3-Hydroxy-4-hydroxymethyl-pyrrolidin-1-yl-methyl]-3,5-dihydro-pyrrolo[3,2-*d*]pyrimidin-4-one (Compound 1) with various organic and inorganic acids. In one embodiment, the organic acid is a C4 organic diacids. The present disclosure further provides novel methods for preparing these salts. The novel monohydrates hemisalts of the C4 organic diacids are isostructural and can be prepared with different properties. Multiple acids can be used simultaneously and the proportion of acids can be varied offering the opportunity to select hemi-salts of compound 1 with desired properties.

5 Claims, 8 Drawing Sheets

Figure 1
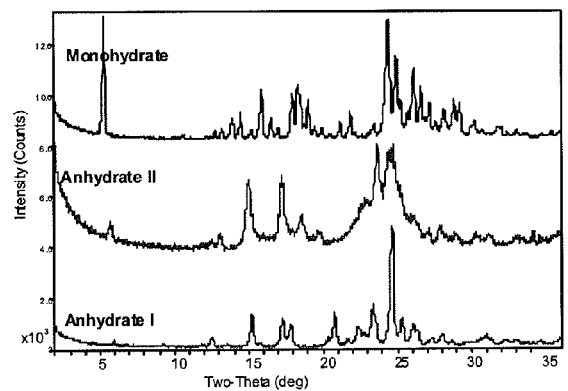
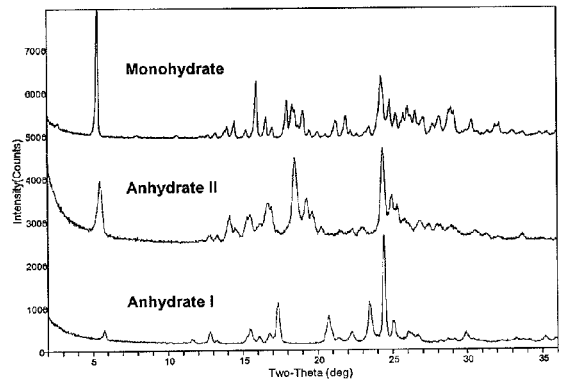
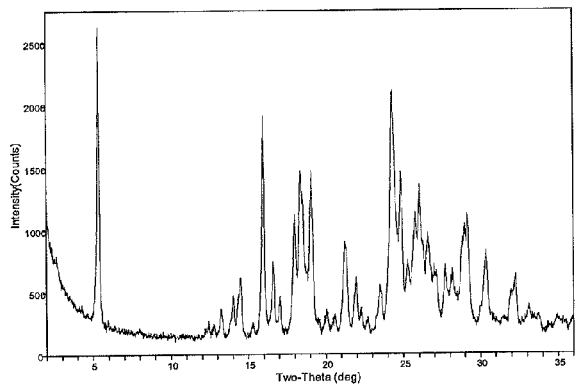

Figure 2
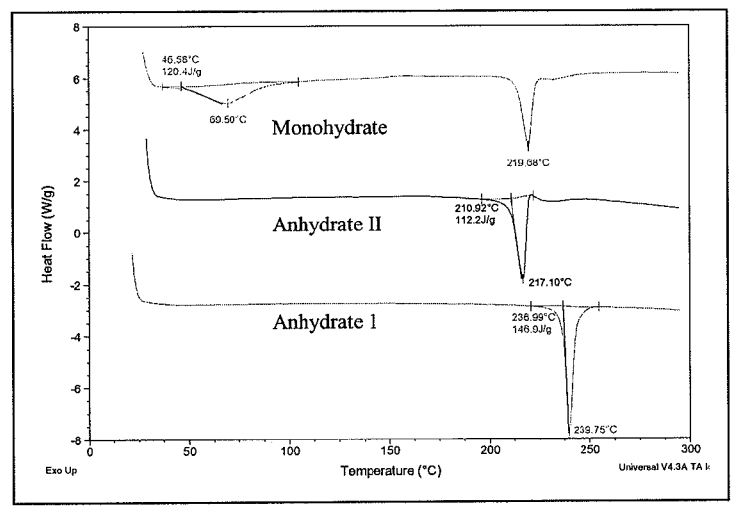
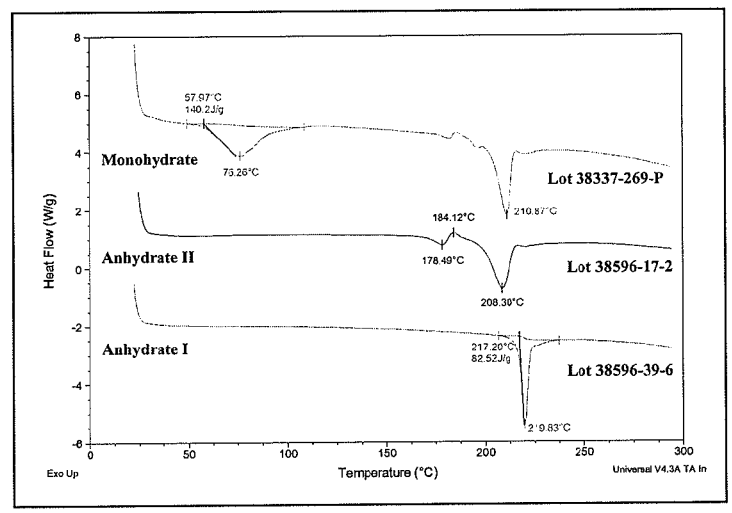

Figure 3- Interconversion Among $C_4$ Dicarboxylic Acid Hemi-salt Forms
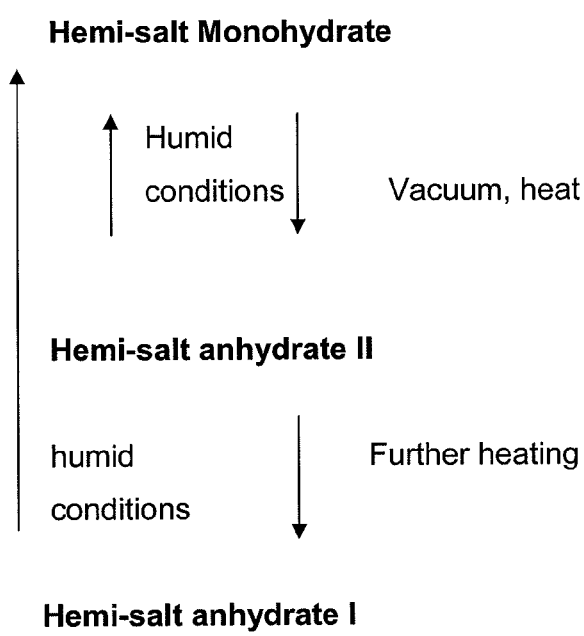

Figure 4- XRPD Traces of Mixed Monohydrate Salts
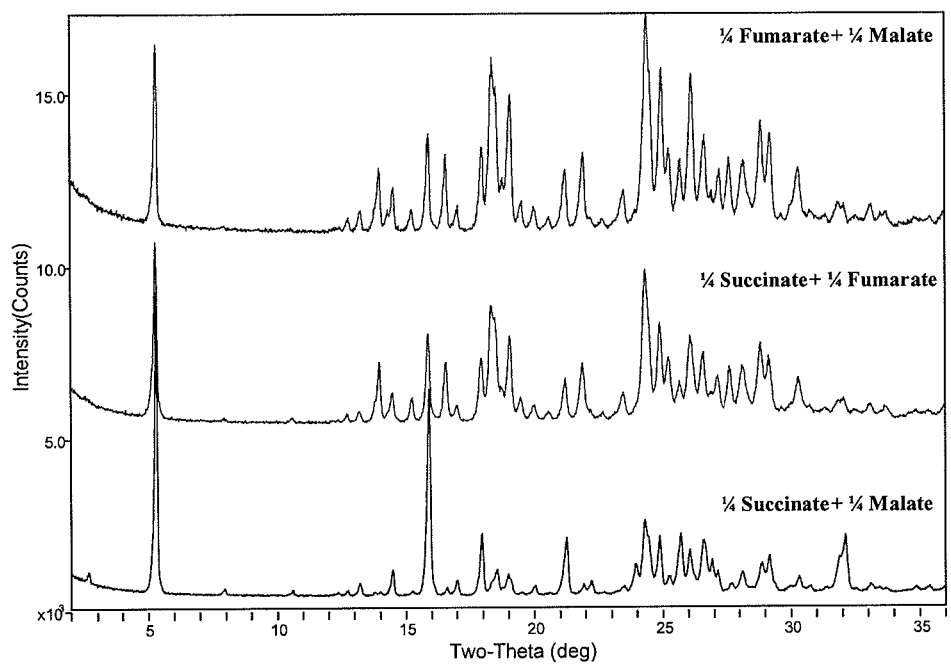

Figure 5- DSC Traces of the Mixed Monohydrate Salts
Hemi-(hemisuccinate, hemimalate) Salt    Hemi-(hemifumarate, hemimalate) Salt
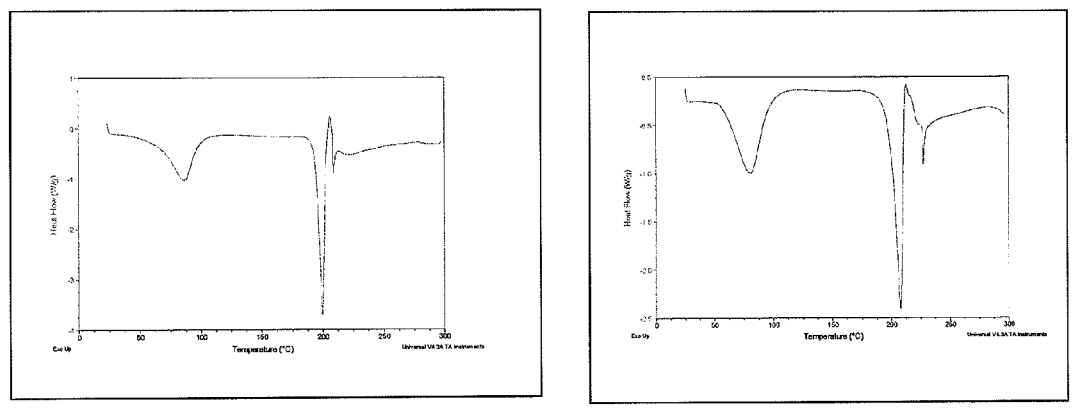
Hemi-(Hemisuccinate, Hemifumarate) Salt    Hemisuccinate and Hemimalate Mixture & Hemi-(Hemisuccinate, Hemimalate) Salt
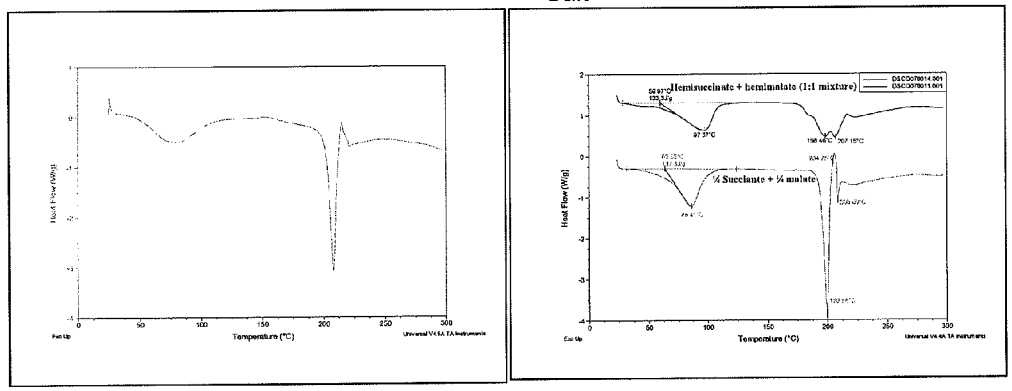

USEFUL PHARMACEUTICAL SALTS OF 7-[(3R, 4R)-3- HYDROXY-4-HYDROXYMETHYL-PYRROLIDIN-1-YLMETHYL]-3, 5-DIHYDRO-PYRROLO [3, 2-D] PYRIMIDIN-4-ONE

FIELD OF THE DISCLOSURE

The present disclosure relates generally to novel salt forms of pharmaceutical compounds and methods of preparing the same. The present disclosure relates specifically to novel salt forms of 7-[(3R,4R)-3-Hydroxy-4-hydroxymethyl-pyrrolidin-1-ylmethyl]-3,5-dihydro-pyrrolo[3,2-d]pyrimidin-4-one (Compound 1) and methods of preparing the same.

BACKGROUND

7-[(3R,4R)-3-Hydroxy-4-hydroxymethyl-pyrrolidin-1-ylmethyl]-3,5-dihydro-pyrrolo[3,2-d]pyrimidin-4-one (Compound 1) inhibits a number of relevant enzymes is implicated in human disease, including, but not limited to, purine nucleoside phosphorylase. 7-[(3R,4R)-3-Hydroxy-4-hydroxymethyl-pyrrolidin-1-ylmethyl]-3,5-dihydro-pyrrolo[3,2-d]pyrimidin-4-one is currently being developed for the treatment of a number of human disease, including, but not limited to cancer, B and T-cell mediated disease, bacterial infections and protozoal infections. The use of Compound 1 is described in U.S. Pat. No. 7,553,839, which is hereby incorporated by reference for such teaching.

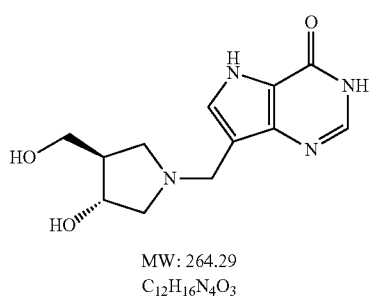

MW: 264.29
$C_{12}H_{16}N_4O_3$

Many pharmaceutically acceptable salts of compound 1 are known in the literature. These include, but are not limited to, hydrochlorides, dihydrochorides, hydrobromides, hemisulfate, p-tosylate, phosphate, citrate, L-tartrate, L-lactate, stearate, maleate, succinate, fumarate, and L-malate.

While a number of salts of compound 1 have been described, many of described salt forms display properties that are not optimal. For example, the hydrochloride salt of compound 1 has been shown to contain polymorphic variants. In certain cases it may be desirable to obtain a salt of a pharmaceutical compound with no or a decreased number of polymorphic variants.

Mixed crystal salts are known in the literature (Kitaigorodsky, A. I., *Solid Solutions*, Springer-Verlag: Berlin, 1984). Mixed crystals are formed when a new molecular entity substitutes for another in a crystal structure without significantly disturbing the unit cell. When the proportion is adjustable in the mixed crystal, the material is also referred to as a solid solution. Most commonly, it is small anions and cations that can substitute for similar species in a crystal lattice. For example, nickel and manganese atoms can substitute for one another to form continuous isomorphic mixed crystals in the double salt $2RbCl.MCl_2.2H_2O$, where M=Ni or Mn (*J. Chem. Thermodynamics*, 28, 743, 1996). Potassium can substitute for rubidium in arenesulfonates (*Inorg. Chem.*, 22, 2924-2931, 1994) and a number of divalent metal ions substitute for one another in formates (*J. Solid State Chem.*, 57, 260-266, 1985).

Less commonly, larger species, such as organic molecules, substitute for one another. For example, progesterones such as 11α-hydroxy-16α, 17α-epoxyprogesterone (HEP) and 16α,17α-epoxyprogesterone (EP) form isostructural mixed crystals up to a certain ratio (*Ind. Eng. Chem. Res.*, 45, 432-437, 2006). Physiologically active sulfadimidine forms monoclinic crystals with either aspirin or 4-aminobenzoic acid and triclinic crystals with either 2-aminobenzoic acid or 4-aminosalicylic acid (*Molecular Pharmaceutics.*, 4 (3), 310-316, 2007). Likewise, cis-itraconazole forms a series of salts with $C_4$ acids (*J. Am. Chem. Soc.*, 125, pp. 8456-8457) which may be isomorphic. U.S. Pat. No. 3,870,732 (1974) teaches that "mixed crystals" of aluminum and certain carboxylic acids can form although it is not clear if they are isomorphic structures.

Mixed salts offer the potential for physical properties that are different from those of the non-mixed salts alone and so can be helpful in many areas such as the manufacturing of drug products, whose suitability for use often hinges on the properties of the active pharmaceutical ingredient. Like unmixed salts, mixed salts are potentially polymorphic and some of these can be expected to be unstable. Therefore it is desirable to develop stable salts that will provide for the easy manufacture of salts of compound 1.

There is a need in the art to develop new salts of compound 1 with new properties. The present disclosure provides novel hemi- and mono-salt forms of compounds 1 and methods of synthesizing the same.

SUMMARY OF THE DISCLOSURE

In a first aspect, the present disclosure provides hemi- and mono-salts of 7-[(3R,4R)-3-Hydroxy-4-hydroxymethyl-pyrrolidin-1-ylmethyl]-3,5-dihydro-pyrrolo[3,2-d]pyrimidin-4-one (Compound 1) having improved properties over salt forms of compound 1 in the prior art.

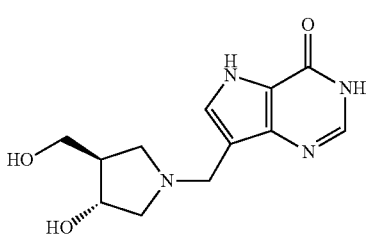

In a second aspect, the present disclosure provides hemi- and mono-salts of compound 1 with organic acids.

In a third aspect, the present disclosure provides hemi- and mono-salts of compound 1 with $C_4$ organic diacids. Exemplary $C_4$ organic diacids include succinic acid, fumaric acid, L-malic acid, maleic acid, L-tartaric acid, L-aspartic acid, or combinations of the foregoing. In one embodiment, the $C_4$ organic diacid is succinic acid, fumaric acid or L-malic acid. In a specific embodiment, the $C_4$ organic diacid is succinic acid.

In a fourth aspect, the present disclosure provides hemi- and mono-salts of compound 1 with $C_4$ organic diacids that exhibit no polymorphic variants or a reduced number of polymorphic variants as compared to the hydrochloride salt of compound 1 or the salt forms of compound 1 known in the art. In one embodiment, the $C_4$ organic diacid is succinic acid and the salt of compound 1 is the hemisuccinate monohydrate salt.

In a fifth aspect, the present disclosure provides hemi-salts of compound 1 with mixed $C_4$ organic diacids. Exemplary combinations of $C_4$ organic diacids for mixed salts of compound 1 include combinations of succinic acid, fumaric acid and L-malic acid. In a specific embodiment, the combinations of $C_4$ organic diacids are succinic acid and fumeric acid, succinic acid and L-malic acid, fumeric acid and L-malic acid and succinic acid, fumeric acid and L-malic acid.

In a sixth aspect, the present disclosure provides hemi- and mono-salts of compound 1 with $C_4$ inorganic acids. Exemplary inorganic acids include phosphoric acid, hydrobromic acid, paratoluene sulfonic acid and sulfuric acid.

In a seventh aspect, the present disclosure provides methods for preparing a salt of compound 1 wherein the salt of compound 1 is a hemi- or mono-salt with an organic acid.

In an eighth aspect, the present disclosure provides methods for preparing a salt of compound 1 wherein the salt of compound 1 is a hemi- or mono-salt with a $C_4$ organic diacid. Exemplary $C_4$ organic diacids include succinic acid, fumaric acid, L-malic acid, maleic acid, L-tartaric acid and L-aspartic acid. In one embodiment, the $C_4$ organic diacid is succinic acid, fumaric acid or L-malic acid. In a specific embodiment, the $C_4$ organic diacid is succinic acid.

In a ninth aspect, the present disclosure provides methods for preparing a salt of compound 1 wherein the salt of compound 1 is a hemi- and mono-salts of compound 1 with $C_4$ organic diacids that exhibit no polymorphic variants or a reduced number of polymorphic variants as compared to the hydrochloride salt of compound 1 or the salt forms of compound 1 known in the art. In one embodiment, the $C_4$ organic diacid is succinic acid and the salt of compound 1 is the hemisuccinate monohydrate salt.

In a tenth aspect, the present disclosure provides methods for preparing a salt of compound 1 wherein the salt of compound 1 is a hemi-salt of compound 1 with mixed $C_4$ organic diacids. Exemplary combinations of $C_4$ organic diacids for mixed salts of compound 1 include combinations of succinic acid, fumaric acid and L-malic acid. In a specific embodiment, the combinations of $C_4$ organic diacids are succinic acid and fumeric acid, succinic acid and L-malic acid, fumeric acid and L-malic acid and succinic acid, fumeric acid and L-malic acid.

In an eleventh aspect, the present disclosure provides methods for preparing a salt of compound 1 wherein the salt of compound 1 is a hemi- or mono-salt with an inorganic acid. Exemplary inorganic acids include phosphoric acid, hydrobromic acid, paratoluene sulfonic acid and sulfuric acid.

DESCRIPTION OF THE FIGURES

FIG. 1 provides the XRPD plots of the hemifumarate, hemisuccinate, and the hemimalate salt forms of compound 1.

FIG. 2 provides DSC plots of the hemifumarate and hemisuccinate salt forms of compound 1.

FIG. 3 illustrates the interconversion among the monohydrates and anhydrates of the $C_4$ dicarboxylic acid hemi-salt forms of compound 1.

FIG. 4 provides the PXRD plots of the three mixed salts of compound 1.

FIG. 5 provides the DSC traces of mixed salts of compound 1. These salts include a hemi-(hemisuccinate, hemimalate) salt, a hemi-(hemifumarate, hemimalate) salt, a hemi-(hemisuccinate, hemifumarate) salt, and a hemisuccinate and hemimalate mixture.

DETAILED DESCRIPTION

Figure 6:
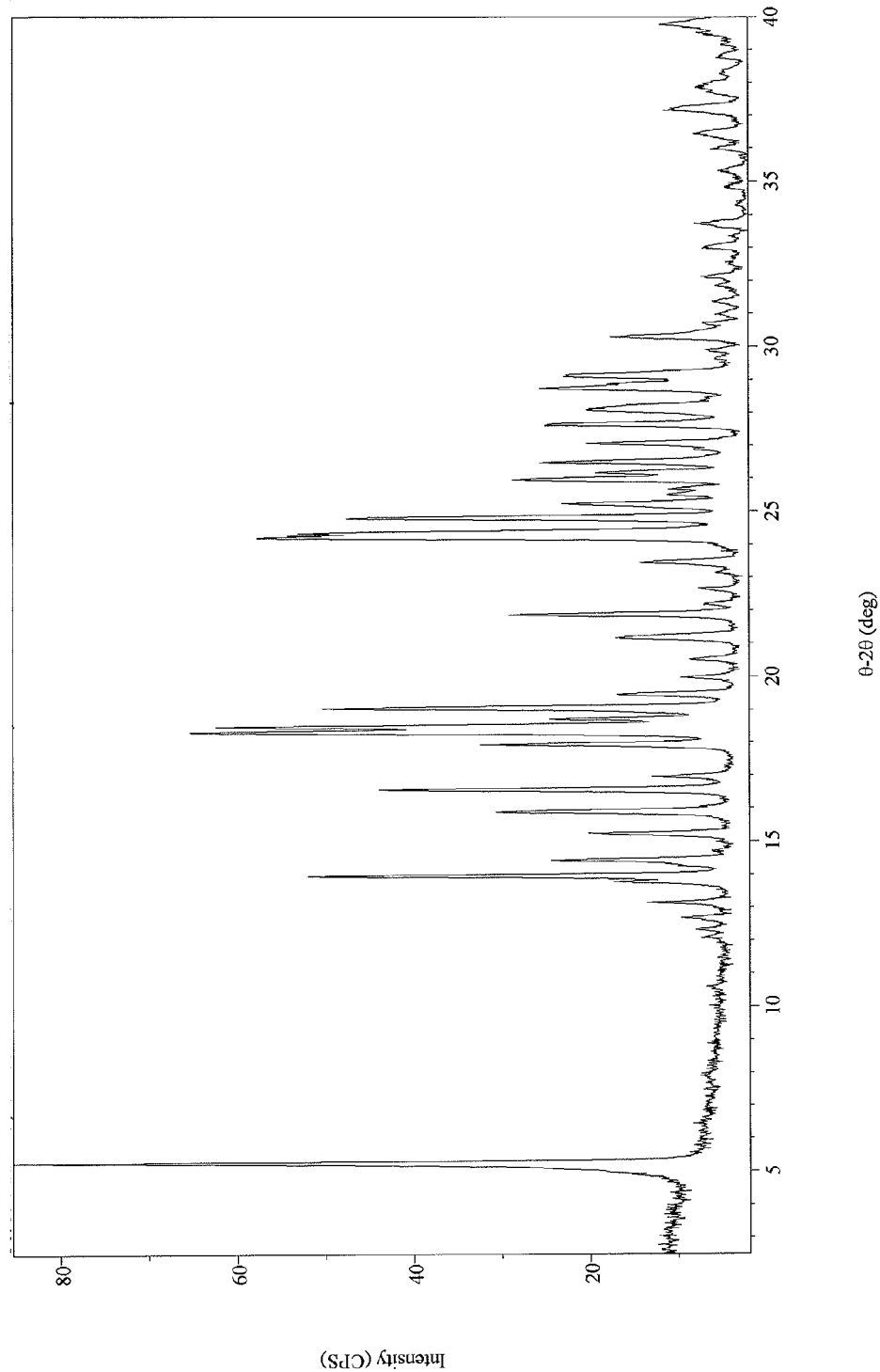
FIG. 6 provides the XRPD plots of the hemisuccinate salt forms of compound 1.
Figure 7:
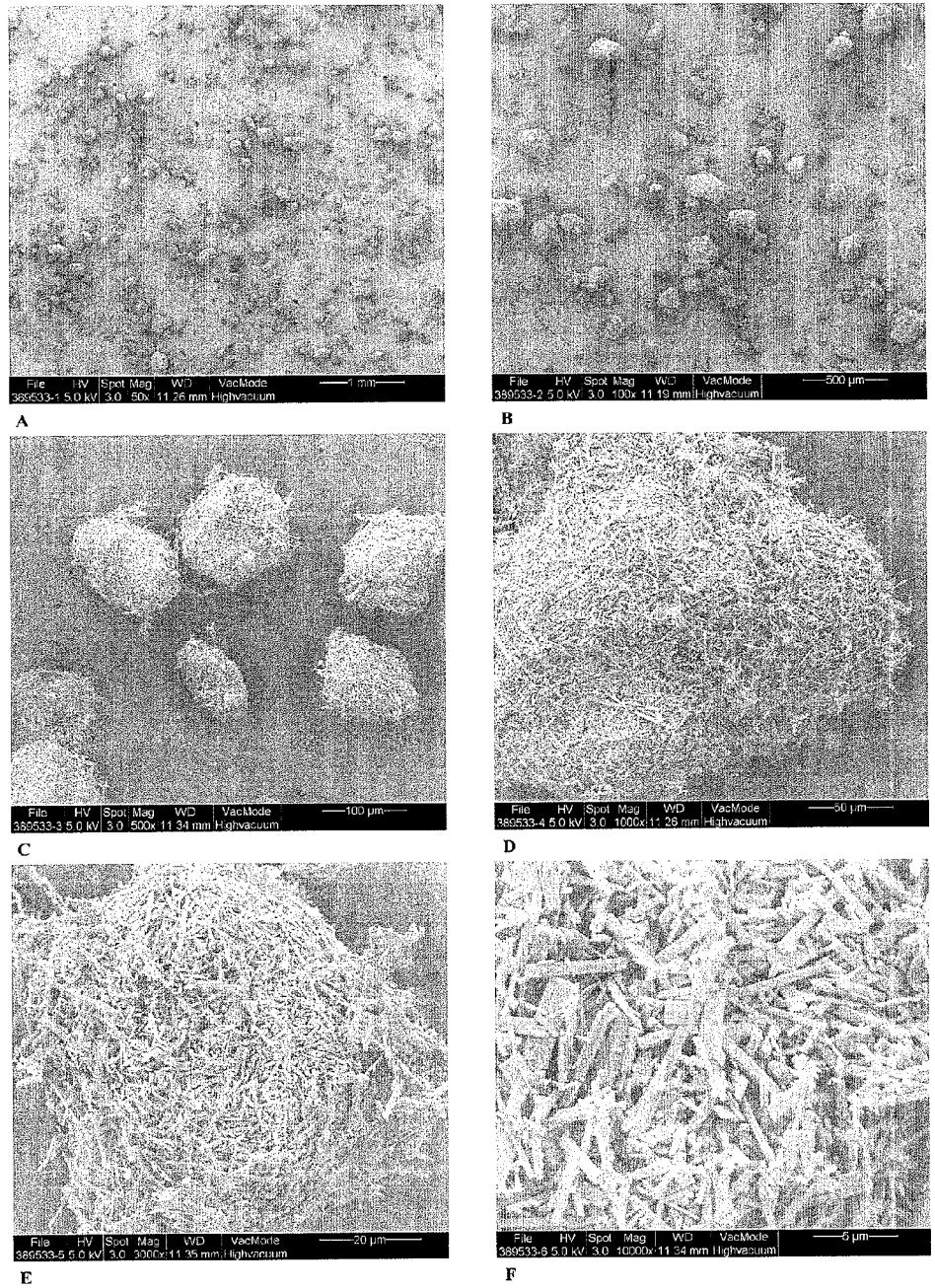
FIG. 7 provides scanning electron micrographs of the hemisuccinate salt forms of compound 1.

As used herein, the following terms have the meanings set out below.

The term "API" refers to the active pharmaceutical ingredient.

The term "hemi" means the ratio of API:acid (whether organic or inorganic) is 2:1, respectively, in the crystal structure of the salt of compound 1. In the case of the hemisuccinate salt of compound 1, for example, the nitrogen atom in the pyrrolidine ring is protonated (as shown by the single crystal structure of the mono-acetate salt) and both carboxylic acid groups of succinic acid are deprotonated. Hence, there are two base molecules of compound 1 and one acid molecule of a $C_4$ organic diacid in the same unit cell with the acid acting as a bridge between them.

The term "inert organic solvent" refers to a solvent that does not interfere chemically with the reaction.

The term "isostructural" is used to describe crystalline substances that have the same type of crystalline structure such as when a new molecular entity substitutes for another in a crystal structure without significantly disturbing the unit cell.

The term "mono" means the ratio of API:acid (whether organic or inorganic) is 1:1, respectively, in the crystal structure of the salt of compound 1. In the case of the mono-acid salt of a $C_4$ organic diacid of compound 1, for example, one carboxylic group of the $C_4$ organic diacid forms a salt with the nitrogen atom in the pyrrolidine ring of compound 1. The other carboxylic acid group may or may not have H-bonding interaction with other parts of the base molecule of compound 1.

The term "pharmaceutically acceptable," such as pharmaceutically acceptable carrier, excipient, etc., means pharmacologically acceptable and substantially non-toxic to the subject to which the particular compound is administered.

The term "pharmaceutically acceptable salt" refers to conventional acid-addition salts or base-addition salts that retain the biological effectiveness and properties of the compounds of the present disclosure and are formed from suitable non-toxic organic or inorganic acids or organic or inorganic bases. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Sample base-addition salts include those derived from ammonium, potassium, sodium, and quaternary ammonium hydroxides, such as for example, tetramethylammonium hydroxide. Chemical modification of a pharmaceutical compound (i.e., drug) into a salt is a technique practiced by pharmaceutical chemists to obtain improved physical and chemical stability, hydroscopicity, and solubility of compounds. See, e.g., H. Ansel et. al., Pharmaceutical Dosage Forms and Drug Delivery Systems (6$^{th}$ Ed. 1995) at pp. 196 and 1456-1457.

The term "prodrug" refers to compounds, which undergo transformation prior to exhibiting their pharmacological effects. The chemical modification of drugs to overcome pharmaceutical problems has also been termed "drug latentiation." Drug latentiation is the chemical modification of a biologically active compound to form a new compound, which upon in vivo enzymatic attack will liberate the parent compound. The chemical alterations of the parent compound are such that the change in physicochemical properties will affect the absorption, distribution and enzymatic metabolism. The definition of drug latentiation has also been extended to include nonenzymatic regeneration of the parent compound. Regeneration takes place as a consequence of hydrolytic, dissociative, and other reactions not necessarily enzyme mediated. The terms prodrugs, latentiated drugs, and bioreversible derivatives are used interchangeably. By inference, latentiation implies a time lag element or time component involved in regenerating the bioactive parent molecule in vivo.

The term "water-soluble alcohol" refers to a $C_1$-$C_4$ alkyl alcohol.

Salts of Compound 1

The present disclosure provides salts of compound 1 having the formula:

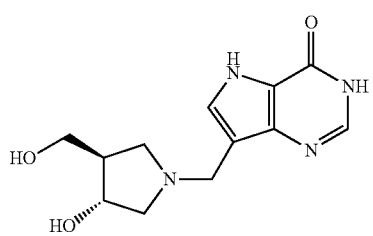

1 wherein the salts of compound 1 are hemi- or mono-salts with an organic acid or an inorganic acid. In a particular embodiment, the present disclosure provides salts of compound 1 wherein the salts are hemi- or mono-salts with one or more $C_4$ organic diacids ($C_4$ dicarboxylic acids). Exemplary $C_4$ organic diacids include, but are not limited to, succinic acid, fumaric acid, L-malic acid, maleic acid, L-tartaric acid, and L-aspartic acid, or combinations of the foregoing. In one embodiment, the $C_4$ organic diacid is succinic acid, fumaric acid, L-malic acid or combinations of the foregoing. In a specific embodiment, the $C_4$ organic diacid is succinic acid.

As set out above, mixed salts can offer different physical properties from non-mixed salts in compounds and so can be helpful in many areas such as the manufacturing of various drugs. Salts of compound 1 vary widely in their suitability for use in drug formulations. In one embodiment, the present disclosure provides mixed salts of compound 1 with $C_4$ organic diacids, which have unexpectedly desirable properties for use in drug formulations of compound 1. Many of the above-mentioned $C_4$ organic diacids exhibit a number of polymorphs.

Many salts of compound 1 can be formed as discussed herein and exemplified in the Examples section. Table 1 below illustrates the X-ray powder diffraction (XRPD), differential scanning calorimetry (DSC), and thermogravimetric analysis (TGA) for certain salts of compound 1. X-ray powder diffraction is a technique used on powder or microcrystalline samples for structural characterization of materials. Differential scanning calorimetry is a thermoanalytical technique in which the difference in the amount of heat required to increase the temperature of a sample and reference are measured as a function of temperature. Thermogravimetric analysis is a type of testing that is performed on samples to determine changes in weight in relation to changes in temperature.

Table 2 below illustrates the X-ray powder diffraction (XRPD), differential scanning calorimetry (DSC), and thermogravimetric analysis (TGA) for selected $C_4$ organic diacids salts of compound 1.

Tables 1 and 2 illustrate that salts of compound 1 show various properties. For manufacturing purposes, the exemplary pharmaceutically acceptable $C_4$ organic diacid salts of compound 1 are selected from the group consisting of succinic, fumaric, L-malic, maleic, L-tartaric, and L-aspartic acids, or combinations of the foregoing. In one embodiment, the $C_4$ organic diacid salts of compound 1 are selected from the group consisting of succinic, fumaric, and L-malic acids or is combinations of the foregoing. In a specific embodiment, the $C_4$ organic diacid salt of compound 1 is succinic acid, specifically the hemisuccinic monohydrate. The above-mentioned $C_4$ organic diacids can form both mono- and hemi-salts with compound 1.

The hemi-salt stoichiometry results in stable, easily manufactured monohydrates, which convert to two anhydrous forms upon heating and drying. These are the most preferred forms. The restoration of moisture leads to a reversion to the original monohydrate. It is noted that the hemisuccinate monohydrate salt of compound 1 does not exhibit polymorps, which can be a desirable property in pharmaceutical manufacturing. Furthermore, the hemisuccinate monohydrate salt of compound 1 exhibits favorable manufacturing characteristics, such as, but not limited to, ease of crystallization and reproducible drying patterns.

The XRPD plots of the hemifumarate, hemisuccinate, and the hemimalate monohydrate salt forms of compound 1 are set out in FIG. 1. The strong similarity between the plots indicates that the monohydrates are isostructural. Since the salts of compound 1 form stable hemi-acid monohydrates and the crystal structures of the salts formed from these acids are isostructural, novel mixed crystalline salts can be prepared having different properties. The ease of preparation suggests that the proportion of acids can be continuously variable and that multiple acids can be used simultaneously. This offers the opportunity to vary the ratio of $C_4$ organic diacids in the crystal structure in order to select the desired properties of the active pharmaceutical ingredient (API).

The data in Tables 1 and 2 and FIGS. 1-5 were taken from salt forms prepare as described in Examples 1-31.

Methods of Preparing Salts of Compound 1

The present disclosure further provides methods for preparing a salt of compound 1 having the formula:

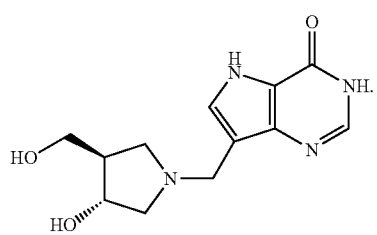

1

Salts of the present disclosure can be formed using acid addition salts, including but not limited to, inorganic and organic acids. In a specific embodiment, the organic acids are $C_4$ organic diacids, such as, but not limited to, L-malic acid, fumeric acid and succinic acid.

In one embodiment, the present disclosure provides methods of preparing a hemi- or mono-salt of the compound 1 with an organic diacid. Three exemplary methods of preparation are provided below (Method 1a, 1b and 1c). Method 1a comprises the steps of:

(a) preparing a slurry of compound 1 free base in a mixture of water and a water-soluble alcohol with heating or in a mixture of an aqueous water-soluble alcohol with heating, such as from about 70° to about 85° C.;

(b) admixing an organic diacid to the mixture from step (a);

(c) heating the mixture from step (b) for a desired period of time, such as from about 70° to about 85° C.;

(d) cooling the mixture from step (c) to about 0° C.±5° C. and adding acetonitrile to the mixture; and (e) filtering the mixture from step (d) to obtain compound 1 as a hemi- or mono-salt with an organic diacid.

Method 1b comprises the steps of:

(a) preparing a slurry of compound 1 free base in a mixture of water and a water-soluble alcohol with heating or in a mixture of an aqueous water-soluble alcohol with heating, such as from about 70° to about 85° C.;

(b) admixing an organic diacid to the mixture from step (a);

(c) adding acetonitrile to the mixture of step (b) and heating the resulting mixture for a desired period of time, such as from about 70° to about 85° C.;

(d) cooling the mixture from step (c) to about 0° C.±5° C.; and (e) filtering the mixture from step (d) to obtain compound 1 as a hemi- or mono-salt with an organic diacid.

Method 1c comprises the steps of:

(a) preparing a slurry of compound 1 free base and an organic diacid in a mixture of water and activated charcoal with heating, such as from about 70° to about 85° C.;

(b) filtering the mixture from step (a) to remove solid particulates and heating is the resulting solution back to a temperature from about 70° to about 85° C.;

(c) adding a hot water-soluble alcohol to the mixture of step (b), holding the resulting solution at a temperature from about 70° to about 85° C. for a desired period of time and allowing the solution to reach ambient temperature; and (d) filtering the mixture from step (c) to obtain compound 1 as a hemi- or mono-salt with a $C_4$ organic diacid The methods above may include holding times after one or more of the steps disclosed. Furthermore, in the methods above, when a heating step is specified, the heating step may comprise cycling the temperature from a higher temperature to a lower temperature two or more times, such as for example, from 80-40-80° C. Still further, in the methods above, when the organic diacid is added it may be added with an amount of the desired final salt form to aid in the crystallization process. In a specific embodiment of the methods above, the organic diacid is a $C_4$ organic diacid, such as, but not limited to, L-malic acid, fumaric acid and succinic acid.

In a further embodiment, the present disclosure provides for methods of preparing a mixed acid hemi-salt with a $C_4$ organic diacid. An exemplary method comprises the steps of:

(a) preparing a slurry of compound 1 free base in a mixture of water and a water-soluble alcohol with heating or in a mixture of an aqueous water-soluble alcohol with heating, such as from about 40° to about 85° C.;

(b) admixing a mixture of organic diacids to the mixture from step (a);

(c) heating the mixture from step (b) for a desired period of time, such as from about 40° to about 85° C.;

(d) cooling the mixture from step (c) to about 0° C.±5° C. and adding acetonitrile to the mixture; and (e) filtering the mixture from step (d) to obtain compound 1 as a hemi-salt with a mixture of $C_4$ organic diacids.

In an alternate method, in step (d), a water-soluble alcohol, such as ethanol, may be substituted for acetonitrile.

The method above may include holding times after one or more of the steps disclosed. Furthermore, in the methods above, when a heating step is specified, the heating step may comprise cycling the temperature from a higher temperature to a lower temperature two or more times, such as for example, from 80-40-80° C. Still further, in the methods above, when the organic diacid is added it may be added with an amount of the desired final salt form to aid in the crystallization process. In a specific embodiment of the methods above, the mixture of organic diacids is two or more of L-malic acid, fumaric acid and succinic acid.

In an alternate embodiment, the present disclosure provides for methods of preparing a hemi- or mono-salt of the compound 1 with organic acids. In one example of this embodiment, the method comprises the steps of:

(a) preparing a slurry of compound 1 free base in a mixture of water and a water-soluble alcohol with heating or in a mixture of an aqueous water-soluble alcohol with heating, such as from about 70° to about 85° C.;

(b) adding an organic acid to the mixture of step (a);

(c) adding acetonitrile to the solution of step (b) and heating the resulting mixture for a desired period of time, such as from about 70° to about 85° C.;

(d) cooling the solution to 0±10° C.; and (e) filtering the mixture from step (d) to obtain compound 1 as a hemi- or mono-salt with an organic acid.

The methods above may include holding times after one or more of the steps disclosed. Furthermore, in the methods above, when a heating step is specified, the heating step may comprise cycling the temperature from a higher temperature to a lower temperature two or more times, such as for example, from 80-40-80° C. In a specific embodiment of the methods above, the organic acid is, for example citric acid, lactic acid, stearic acid or acetic acid.

In a further alternate embodiment, the present disclosure provides for methods of preparing a hemi- or mono-salt of the compound 1 with inorganic acids. Two exemplary methods of preparation are provided below (Method 1d and 1e). Method 1d comprises the steps of:

(a) preparing a slurry of compound 1 free base in a mixture of a water-soluble alcohol under inert conditions and heating the slurry for a desired period of time, such as from about 75° to about 85° C.;

(b) adding water to the slurry of (a) under the same temperature to produce a gently refluxing homogenous solution;

(c) removing the mixture of step (b) from heating and adding an inorganic acid;

(d) heating the solution of step (c) for a desired period of time, such as from about 70° to about 85° C., to produce a gently refluxing solution;

(e) allowing the solution to cool to ambient temperature and incubating for a desired period of time; and (f) filtering the mixture from step (e) to obtain compound 1 as a hemi- or-mono salt with an inorganic acid.

Method 1e comprises the steps of:

(a) preparing a slurry of compound 1 free base in a mixture of a water-soluble alcohol under inert conditions and heating the slurry for a desired period of time, such as from about 75° to about 85° C.;

(b) adding water to the slurry of (a) under the same temperature to produce a gently refluxing homogenous solution;

(c) removing the mixture of step (b) from heating and adding an inorganic acid;

(d) heating the solution of step (c) for a desired period of time, such as from about 75° to about 85° C. C to produce a gently refluxing solution;

(e) allowing the solution to cool to ambient temperature and incubating for a desired period of time; and (f) adding the solution of step (e) dropwise to acetonitrile at ambient temperature;

(g) adding an additional amount of acetonitrile to the solution of step (f); and (h) filtering the mixture from step (g) to obtain compound 1 as a hemi- or mono-salt with an inorganic acid.

The methods above may include holding times after one or more of the steps disclosed. Furthermore, in the methods above, when a heating step is specified, the heating step may comprise cycling the temperature from a higher temperature to a lower temperature two or more times, such as for example, from 80-40-80° C. In a specific embodiment of the methods above, the inorganic acid is phosphoric acid, hydrobromic acid and sulfuric acid.

The compounds of the present disclosure can be prepared according to the examples set out below. The examples are presented for purposes of demonstrating, but not limiting, the preparation of the compounds and compositions of this disclosure.

EXAMPLES

In accordance with the present disclosure, the following examples are provided to illustrate preferred methods for preparing salts of compound 1.
General Methods Unless otherwise indicated in a specific example below, the following general methods were used.
Differential Scanning Calorimetry (DSC)

The DSC data were collected using a DSC Q2000 or a DSC 2920 from TA Instruments. The sample was heated in an aluminum pan at a rate of 10° C./min, up to a final temperature of 300° C.
Thermogravimetry (TGA)

The TGA data were collected using a TGA Q5000IR or a TGA2950 from TA Instruments. The sample was heated in a platinum pan at a rate of 10° C./min, up to a final temperature of 300° C.
X-Ray Powder Diffraction (XRPD)

The X-ray powder diffraction patterns were measured on a Scintag X1 powder X-ray diffractometer equipped with a sealed copper Kα1 radiation source. The samples were scanned from 2° to 36° 2θ at a rate of 1° per minute with incident beam slit widths of 2 and 4 mm and diffracted beam slit widths of 0.5 and 0.2 mm.

Example 1

General Procedure for the Preparation of Salts of Compound 1 with $C_4$ Organic Diacid Hemi-Salts Via Method 1a A general procedure for preparing the $C_4$ organic diacid hemi-salts is set out below. This example is given for the preparation of the hemisuccinate monohydrate, but the same procedure can be used to make the other $C_4$ organic diacid salts, making minor adjustments.

Preparation of Compound 1 Hemisuccinate Monohydrate.

Prepare a slurry of 14.00 grams (53.0 mmol) of compound 1 free base, 10 grams of water, and 200 grams of ethanol. Stir well and heat to 75-80° C. Dissolve 3.44 g (29.1 mmol) of succinic acid in 50 grams of water with a little warming (the $C_4$ organic diacid can also be added neat or in an aqueous alcohol mixture). Add one-fourth of the succinic acid solution to the compound 1 free base slurry and add a few milligrams of compound 1 hemisuccinate monohydrate seeds. Stir for 15 minutes and then add the remaining succinic acid solution over a period of 1 hour at 75°-80° C. Take the batch through two (2) temperature cycles from ~79° C. to ~50° C. and back to ~79° C. Use a ramp rate of 0.2° C./minute. Then cool to 0° C.±5° C. at 0.2° C./minute. A hold time afterward is optional. Add 156 grams of acetonitrile (200 mL) over a 1-hour period. A hold time afterward is optional. Filter and wash with 20 grams of 95:5 acetonitrile: water (w/w %). Dry at 30° C.±5° C. overnight under vacuum. The expected yield is 16.3 grams (90%).

As noted above, mixed crystals were also prepared. These include the hemi(hemisuccinate-hemifumarate) monohydrate, hemi(hemisuccinate-hemimalate) monohydrate, hemi (hemifumarate-hemimalate) monohydrate, and hemi (hemisuccinate-hemifumarate) monohydrates of compound 1. In each case, one-fourth of a mole of each of two acids forms a salt with one mole of the free base. One mole of water is present as water of crystallization.

FIG. 1 provides the XRPD plots of the hemifumarate, hemisuccinate, and the hemimalate salt forms of compound 1.

FIG. 2 provides DSC plots of the hemifumarate and hemisuccinate salt forms of compound 1.

FIG. 3 illustrates the interconversion among the monohydrates and anhydrates of the $C_4$ dicarboxylic acid hemi-salt forms of compound 1. The temperatures required to dehydrate the monohydrate varies among the salts are not shown.

FIG. 4 provides the XRPD plots of the three mixed salts of compound 1. The plots display very similar peaks indicating a common unit cell.

FIG. 5 provides the DSC traces of mixed salts of compound 1. These salts include a hemi-(hemisuccinate, hemimalate) salt, a hemi-(hemifumarate, hemimalate) salt, a hemi-(hemisuccinate, hemifumarate) salt, and a hemisuccinate and hemimalate mixture The DSC patterns are clearly different and provide more evidence that the mixed salt is pure substance and not merely a physical mixture of salts. The ease of preparation shows that the proportion of acids can be continuously variable and that multiple acids can be used simultaneously. This allows the possibility of adjusting the acid proportions in order to fine-tune the desired physical properties of the active pharmaceutical ingredient.

TGA data indicates a loss of about 5% water for each of the salts. This is consistent with a monohydrate.

The following examples illustrate the preparation of pharmaceutically useful salts of compound 1 from Table 1.

Example 2

Free Base of Compound 1

7.0 grams (26.5 mmol) of Free base was charged to a reactor with 100 grams of ethanol and 25 grams of water. The contents were warmed to 80° C. to form a homogeneous solution. 300 ml of Acetonitrile was added over a 20 minute interval to form a slurry. The temperature part way through the addition dropped, due to a lower boiling point, to about 74° C. The slurry was then cooled to 0° C. over 3.5 hours. The solids were filtered and dried at 50° C. in a vacuum oven. The recovery from this purification operation was 82.9%, 5.8 grams.

Example 3

Phosphate of Compound 1

To a parallel reactor tube and heating block apparatus (Radleys Discovery Technologies, Model RR98072) containing a magnetic stir bar was charged 500 mg (1.89 mmol, 1.0 eq.) of compound 1 free base. After inerting with nitrogen, 9.1 mL of ethanol was charged and with stirring the mixture was heated to reflux by adjusting the heating block to 79° C. The resulting slurry was dissolved by the addition of 1.75 mL of deionized water to afford a gently refluxing homogeneous solution. The reaction tube was briefly removed from the heating block to temporarily reduce the refluxing followed by the addition of 0.11 mL (1.89 mmol, 1.0 eq.) of phosphoric acid with stirring. After placing the tube back into the heating block, the solution was stirred at reflux for 15 minutes to 1 hour, then the heating block was turned off and the resulting solution was allowed to cool to ambient temperature with stirring. After 25 hours oiling out was visually observed. After a total of 3 days, the resulting solids, which had formed, were isolated by suction filtration and dried under vacuum at 35° C. for 13 hours to afford 576 mg (84% yield) of an oily solid.

Example 4

Citrate of Compound 1

7.0 grams (26.5 mmol) of Free base was charged to a reactor with 100 grams of ethanol and 25 grams of water. The contents were warmed to 75° C. to form a homogeneous solution. 5.09 grams (26.5 mmol) of citric acid was added. 300 ml of acetonitrile was added over a 30 minute interval. The slurry was then cooled to 0° C. over 1 hour. Since clumps were present instead of uniform crystals, the heater/chiller unit was programmed to take the internal temperature from 0° C. to ~35° C. over a 2-hour period, followed by a slow 10-hour cool to 0° C., and a hold of 2 days at 0° C. The resulting solids were filtered and dried at 50° C. in a vacuum oven. The yield was 66.9%, 8.8 g.

Example 5

L-Tartrate of Compound 1

7.0 grams (26.5 mmol) of Free base was charged to a reactor with 100 grams of ethanol and 25 grams of water. The contents were warmed to 80° C. to form a homogeneous solution. 3.98 grams (26.5 mmol) of L-tartaric acid was added. 300 ml of acetonitrile was added over a -hour interval. The slurry was then cooled to 0° C. over 3 hours. Since an oil formed instead of uniform crystals, the contents of the reactor were stripped until only an oil and a small amount of solvent remained. 8 ml of water was added which dissolved the oil. 250 ml of acetonitrile was added whereupon the oil reformed. Half of the solvent was stripped from the vessel. The contents of the vessel were allowed to cool to room temperature overnight. Overnight solids formed. The reactor was re-heated to 40° C., 200 ml of acetonitrile was added and the contents were cooled to −5° C. at 0.1° C./minute. The resulting solids were filtered and dried at 50° C. in a vacuum oven. The yield was 67.4%, 7.4 g.

Example 6

Maleate of Compound 1

7.0 grams (26.5 mmol) of Free base was charged to a reactor with 100 grams of ethanol and 25 grams of water. The contents were warmed to 80° C. to form a homogeneous solution. 3.07 grams (26.4 mmol) of maleic acid was added. 300 ml of acetonitrile was added over a 1-hour interval. The temperature part way through the addition dropped, due to a lower boiling point, to about 75° C. The slurry was then cooled to 0° C. over about 2 hours. Since no solids had formed, 205 ml of acetonitrile was added. No change was observed. 200 ml of solvent was stripped from the vessel at room temperature. 110 ml of acetonitrile was added. Solids developed. The temperature was first raised to about 50° C. and then reduced to 0° C. over 2 hours. The solids were filtered and dried at 50° C. in a vacuum oven. The yield was 72.1%, 7.26 g.

Example

L-Lactate of Compound 1

7.0 grams (26.5-mmol) of Free base was charged to a reactor with 100 grams of ethanol and 25 grams of water. The contents were warmed to 80° C. to form a homogeneous solution. 2.39 grams (26.5 mmol) of L-lactic acid was added. 300 ml of acetonitrile was added over a 1-hour interval. The temperature part way through the addition dropped, due to a lower boiling point, to about 75° C. The slurry was then cooled to 0° C. over about 2 hours. Since no solids had formed, the temperature was reduced to −9° C. Solids formed and were filtered and dried at 50° C. in a vacuum oven. The yield was 74.0%, 6.95 g.

Example 8

Stearate of Compound 1

7.0 grams (26.5 mmol) of Free base was charged to a reactor with 100 grams of ethanol and 25 grams of water. The contents were warmed to 80° C. to form a homogeneous solution. 7.54 grams (26.5 mmol) of stearic acid was added. 300 ml of Acetonitrile was added over a 1-hour interval. The temperature dropped to 77° C. The temperature was reduced to 0° C. over 2 hours. Solids formed and were filtered and dried at 50° C. in a vacuum oven. The yield was 83.3%, 12.1 g.

Example 9

HBr of Compound 1

To a parallel reactor tube and heating block apparatus (Radleys Discovery Technologies, Model RR98072) containing a magnetic stir bar was charged 500 mg (1.89 mmol, 1.0 eq.) of compound 1 free base. After inerting with nitrogen, 9.1 mL of ethanol was charged and with stirring the mixture was heated to reflux by adjusting the heating block to 79° C. The resulting slurry was dissolved by the addition of 1.75 mL of deionized water to afford a gently refluxing homogeneous solution. The reaction tube was briefly removed from the heating block to temporarily reduce the refluxing followed by the addition of 0.34 mL (1.89 mmol, 1.0 eq.) of 33% HBr in acetic acid with stirring. After placing the tube back into the heating block, the solution was stirred at reflux for 15 minutes to 1 hour, then the heating block was turned off and the resulting solution was allowed to cool to ambient temperature with stirring. After 3 days, the resulting fine white solids were isolated by suction filtration and dried under vacuum at 35° C. for 13 hours to afford 449 mg (69% yield) of a white solid (DSC analysis: 1 minimum@234.8° C.).

Example 10

Tosylate of Compound 1

To a parallel reactor tube and heating block apparatus (Radleys Discovery Technologies, Model RR98072) containing a magnetic stir bar was charged 500 mg (1.89 mmol, 1.0 eq.) of compound 1 free base. After inerting with nitrogen, 9.1 mL of ethanol was charged and with stirring the mixture was heated to reflux by adjusting the heating block to 79° C. The resulting slurry was dissolved by the addition of 1.75 mL of deionized water to afford a gently refluxing homogeneous solution. The reaction tube was briefly removed from the heating block to temporarily reduce the refluxing followed by the addition of 360 mg (1.89 mmol, 1.0 eq.) of p-toluenesulfonic acid, monohydrate with stirring. After placing the tube back into the heating block, the solution was stirred at reflux for 15 minutes to 1 hour, then the heating block was turned off and the resulting solution was allowed to cool to ambient temperature with stirring. After 4 days, the homogeneous solution was added dropwise to 23 mL of stirring acetonitrile at ambient temperature, causing cloudiness, which redissolved near the end of the addition. The resulting solution was further diluted with 10 mL of acetonitrile and after 15 minutes a white slurry had formed. After 4 hours at ambient temperature, the resulting white solids were isolated by suction filtration and dried under vacuum at 35° C. for 19 hours to afford 467 mg (57% yield) of a white solid (DSC analysis: 1 minimum@202.2° C.).

Example 11

Acetate of Compound 1

7.0 grams (26.5 mmol) of Free base was charged to a reactor with 100 grams of ethanol and 25 grams of water. The contents were warmed to 80° C. to form a homogeneous solution. 1.60 grams (26.6 mmol) of acetic acid was added. 300 ml of acetonitrile was added over a 30 minute interval. The temperature dropped to 76° C. The temperature was reduced to 0° C. over 3.5 hours. Solids formed and were filtered and dried at 50° C. in a vacuum oven. The yield was 78.0%, 6.7 g.

Example 12

Hemisulfate of Compound 1

7.0 grams (26.5 mmol) of Free base was charged to a reactor with 100 grams of ethanol and 25 grams of water. The contents were warmed to 80° C. to form a homogeneous solution. 1.30 grams (13.3-mmol) of sulfuric acid was added. 300 ml of acetonitrile was added over a 1-hour interval. The temperature dropped to 75° C. The temperature was reduced to −2° C. over 2 hours. Solids formed and were filtered. Drying was done at 50° C. in a vacuum oven. The yield was 68.8%, 6.6 g.

Example 13

Monofumarate of Compound 1

7.0 grams (26.5 mmol) of Free base was charged to a reactor with 100 grams of ethanol and 25 grams of water. The contents were warmed to 80° C. to form a homogeneous solution. 3.08 grams (26.5 mmol) of fumaric acid was added. 300 ml of Acetonitrile was added over a 30 minute interval. The temperature dropped to 75° C. The temperature was reduced to 0° C. over 2 hours. Solids formed and were filtered. Drying was done at 50° C. in a vacuum oven. The yield was 67.5%, 6.8 g.

Example 14

Monosuccinate of Compound 1

14.0 grams (53.0 mmol) of Free base was charged to a reactor with 300 grams of 80% aqueous ethanol by weight. The contents were warmed to 80° C. to form a homogeneous solution. 8.26 grams (69.9 mmol) of Succinic acid was added. 600 ml of Acetonitrile was added over a 30 minute interval. The temperature dropped to 75° C. The temperature was reduced to 0° C. over 2.5 hours. Solids formed and were filtered. Drying was done at 50° C. in a vacuum oven. The yield was 94.4%, 19.13 g.

Example 15

Hemi-L-Malate Monohydrate of Compound 1

10.0 grams (37.8 mmol) of Free base was charged to a reactor with 142.9 grams of ethanol and 7.1 grams of water. The contents were warmed to 80° C. to form a homogeneous solution. 5.1 grams (38.0 mmol) of L-malic acid dissolved in 35.7 grams of water was added over a 1-hour interval.

At this point, it was decided to attempt to make the hemimalate. Accordingly, 10 grams (37.8 mmol) of additional free base was added. Solids began to form. To improve the crystal quality, acetonitrile was not added. Instead a series of temperature cycles were initiated. The temperature was reduced to ~45° C. over 200 minutes then increased to ~80° C., then back to 45° C. over 200 minutes, to 80° C. over 200 minutes, and finally to 0° C. over 465 minutes. 143 ml of Acetonitrile was added over a 1-hour period. The solids were washed with a little 95% aqueous acetonitrile and dried at 30° C. in a vacuum oven. The yield was 81.7%, 26.44 g.

The following examples illustrate the preparation of pharmaceutically useful salts of compound 1 from Table 2.

Example 16

Hemisuccinate Monohydrate of Compound 1

14.0 grams (53.0 mmol) of Free base was charged to a reactor with 300 grams of 80% aqueous ethanol by weight. The contents were warmed to 80° C. to form a homogeneous solution. 6.26 grams (53.0 mmol) of succinic acid was added. 600 ml of acetonitrile was added over a 46 minute interval. The temperature dropped to 75° C. The batch was held for one hour. The temperature was then reduced to 0° C. over 2.5 hours. Solids formed and were filtered. Drying was done at 50° C. in a vacuum oven. The yield was 93.2%, 16.85 g.

Example 17

Hemisuccinate Monohydrate of Compound 1

14.0 grams (53.0 mmol) of Free base was charged to a reactor with 300 grams of 80% aqueous ethanol by weight. The contents were warmed to 80° C. to form a homogeneous solution. 3.13 grams (26.5 mmol) of succinic acid was added. 600 ml of Acetonitrile was added over a 1-hour interval. The temperature dropped to 74° C. The batch was held for one hour. The temperature was then reduced to 0° C. over 5 hours. Solids formed and were filtered. Drying was done at 50° C. in a vacuum oven. The yield was 90.0%, 16.28 g.

Example 18

Hemisuccinate Anhydrate I of Compound 1

3 grams (8.8 mmol) of Hemisuccinate monohydrate were suspended in 2 ml ethanol at 60° C. for 8 h. The solids were filtered and dried.

Example 19

Hemisuccinate Anhydrate II of Compound 1

20 mg (58.6 mmol) of Hemisuccinate monohydrate was filled into an aluminum DSC pan. The pan was heated to 130° C. and kept in isotherm for 40 minutes in a DSC cell. Then the DSC cell was cooled to room temperature and the solids were removed for the DSC pan.

Example 20

Hemifumarate Monohydrate of Compound 1

This form was prepared by a number of methods. For example, slow evaporation of the monofumarate in 1:6 water:dioxane or 1:8 water:IPA, slow cooling from 1:8 water:IPA starting at 60° C., or equilibration in 1:5 water:tetrahydrofuran at room temperature for 13 days.

Example 21

Hemifumarate Anhydrate I of Compound 1

14.0 grams (53.0 mmol) of Free base was charged to a reactor with 300 grams of 80% aqueous ethanol by weight. The contents were warmed to 80° C. to form a homogeneous solution. 6.16 grams (53.1 mmol) of Fumaric acid was added. 600 ml of acetonitrile was added over a 1-hour interval. The temperature dropped to 75° C. The batch was held for one hour. The temperature was then reduced to 0° C. over 2.5 hours. Solids formed and were filtered. Drying was done at 50° C. in a vacuum oven. The yield was 98.3%, 16.79 g.

Example 22

Hemifumarate Anhydrate II of Compound 1

10.0 grams (37.8 mmol) of Free base and 42.9 grams of water were heated to 75° C. 2.20 grams (19.0-mmol) of fumaric acid was added. The resulting solution was cooled to 20° C. and 34.5 grams of ethanol was added. A small amount of hemifumarate monohydrate seeds were added. Crystallization began. 430 mL of Acetonitrile was added over 1.5 hours. The mixture was cooled to 0° C., filtered, and dried at 30° C. The wet cake was the hemifumarate monohydrate form, but after drying it had converted to the anhydrate form designated anhydrate II.

Example 23

Hemifumarate Anhydrate II of Compound 1

20 mg (0.1 mmol) of Hemifumarate monohydrate was filled into an aluminum DSC pan. The pan was heated to 150° C. and kept in isotherm for 40 minutes in a DSC cell. Then the DSC cell was cooled down to room temperature and the solids were removed for the DSC pan.

Example 24

Monofumarate of Compound 1

To a parallel reactor tube and heating block apparatus (Radleys Discovery Technologies, Model RR98072) containing a magnetic stir bar was charged 500 mg (1.89 mmol, 1.0 eq.) of compound 1 free base. After inerting with nitrogen, 9.1 mL of ethanol was charged and with stirring the mixture was heated to reflux by adjusting the heating block to 79° C. The resulting slurry was dissolved by the addition of 1.75 mL of deionized water to afford a gently refluxing homogeneous solution. The reaction tube was briefly removed from the heating block to temporarily reduce the refluxing followed by the addition of 219 mg (1.89 mmol, 1.0 eq.) of fumaric acid with stirring. After placing the tube back into the heating block, the solution was stirred at reflux for 15 minutes to 1 hour, then the heating block was turned off and the resulting solution was allowed to cool to ambient temperature with stirring. After 3 days, the resulting slurry was diluted by the addition of 11.5 mL of acetonitrile and isolated by suction filtration and dried under vacuum at 35° C. for 13 hours to afford 525 mg (73% yield) of a white solid.

Example 25

Hemi(Hemisuccinate-Hemifumarate) Monohydrate of Compound 1

13.66 grams (51.7 mmol) of Free base, 10 grams of water, and 201.5 grams of ethanol were charged to a reactor and heated to 80° C. A solution of 1.71 grams (14.7 mmol) of fumaric acid, 1.75 grams (14.8 mmol) of succinic acid, 50 grams of water, and 50 grams of ethanol were charged to the reactor. The temperature was cycled from 80° C. to 40° C. and back to 80° C. two times and then cooled to 0° C. at 0.2° C./minute. 160 grams of ethanol was charged. The batch was filtered one hour later. The cake was rinsed with a little 95% (w/w %) aqueous ethanol, and dried at 30° C. under vacuum. 15.8 grams of product were obtained for a yield of 89.7%.

Example 26

Hemi(Hemisuccinate-Hemi-L-Malate) Monohydrate of Compound 1

14.0 grams (53.0 mmol) of Free base, 10 grams of water and 201 grams of ethanol were heated to 76° C. A solution of 1.97 grams (14.7 mmol) of malic acid, 1.77 grams (15.0 mmol) of succinic acid, and 50 grams of water was added to the reactor. The temperature was cycled from 80° C. to 40° C. and back to 80° C. two times and then cooled to 0° C. at 0.2° C./minute. 159 grams of Ethanol was charged over a 30 minute period. The batch was filtered one-half hour later. The cake was rinsed with a little 95% (w/w %) aqueous ethanol, and dried at 30° C. under vacuum. 16.3 grams of product were obtained for a yield of 89.1%.

Example 27

Hemi(Hemifumarate-Hemi-L-Malate) Monohydrate of Compound 1

14.0 grams (53.0 mmol) of Free base, 10 grams of water and 125 grams of ethanol were heated to 76° C. A solution of 1.69 grams (14.6-mmol) of fumaric acid, 1.95 grams (14.5 mmol) of malic acid, 75 grams of ethanol, and 50 grams of water was added to the reactor. The temperature was cycled from 80° C. to 40° C. and back to 80° C. two times and then cooled to 0° C. at 0.2° C./minute. Since the slurry did not appear entirely crystalline, the slurry was heated to about 60° C. and cycled twice from 60° C. to about 25° C. and back to 60° C. twice and then cooled to −2° C., all at 0.2° C./minute. 159 grams of ethanol was charged over a 30 minute period. The batch was filtered one-half hour later and air-dried. 16.34 grams of product were obtained for a yield of 89.5%.

The following examples illustrate the preparation of additional pharmaceutically useful salts of compound 1.

Example 28

Hemisuccinate Monohydrate of Compound 1

1,125 grams (4.26 mol) of Free base was charged to a reactor with 804 grams of water and 16,100 grams of ethanol. The contents of the reactor were warmed to 74° C. A solution of 277 grams (2.35 mol) of succinic acid and 4,016 grams of water was added over a 1-hour period. Temperature cycling of the resulting slurry was started. The batch at 74° C. was cycled twice from 74° C. to about 45° C. and back to 74° C. twice, and then cooled to 0° C., all at 0.2° C./minute. 12.5 kg of Acetonitrile was added over a 1-hour interval. The batch was held for one hour and then filtered. The cake was washed with 1.6 liters of 95% aqueous acetonitrile. Drying was effected at 30° C. in a vacuum oven. The yield was 95.6%, 1388 grams Example 29

Hemifumarate Monohydrate of Compound 1

65 mg (0.2 mmol) of Hemifumarate anhydrate was dissolved in 4 ml of isopropanol and 1.2 ml of H$_2$O. The solution was filtered to a vial that was placed into a bigger vial filled with acetone. The monohydrate crystals produced by vapor-diffusion were filtered and dried.

Example 30

Hemifumarate Anhydrate I of Compound 1

14.0 grams (53.0 mmol) of Free base and 300 grams of 80% (w/w %) aqueous ethanol were heated to 79° C. 3.07 grams (26.4 mmol) of fumaric acid was added. 600 ml of Acetonitrile was added over a 1-hour period. The temperature dropped to 74° C. due to the reduced reflux temperature. The temperature was reduced to −2° C. over 3 hours and held overnight. After filtration and drying at 50° C., a 97.4% yield, 16.62 grams were obtained.

Example 31

Hemi(Hemisuccinate-Hemifumarate) Monohydrate of Compound 1

500 mg (1.5 mmol) of partially dehydrated monohydrate form was suspended in 1 ml H$_2$O at room temperature for 4 hours. The solids were filtered and dried.

Example 32

Hemisuccinate Monohydrate of Compound 1

205.07 g of wet Free base and 50.49 g of succinic acid was charged to a 2.0 L reaction vessel with overhead stirrer and temperature controller with 512.7 mL of water (2.5 equivalents of the estimated dried weight of the API free base) and 4.1 g of activated charcoal (2% of the estimated dried weight of the API free base). The contents of the reactor were stirred and warmed to 70-75° C. where it was held for 30 min. The hot mixture was filtered through a bed of Celite wet with hot water and washed with hot water (105 mL, ~70-75° C., 0.5 equivalents of the estimated dried weight of the free base for a total of 3.0 eq. of water). The resulting solution was heated back to 70-75° C. To the hot water solution were slowly added 1455.6 mL of hot ethanol (~70-75° C., for a total of 9.0 equivalents of the estimated dried weight of the free base). The difference between the amounts added now and the total is the amount of ethanol in the wet sample). Following the addition, the solution is held at 70-75° C. for 5-10 minutes then allowed to reach ambient temperature in about 4-5 h with strong stirring.

The slurry is then filtered under high vacuum in a Buchner funnel. The resulting cake is washed with 1320 ml ethanol/water solution 95:5 vol/vol (3× using 440 ml each time and turning on/off the vacuum pump between washes to ensure proper mixing). The cake is dried in a vacuum oven at 30° C. and >30 in. of Hg until constant weight is obtained (12-18 h). The yield was 92% with a purity of 99.6827 (area %).

XRPD data were obtained on the salt in this example and shown in FIG. 6. The XRPD pattern displays sharp peaks indicating crystalline material. The XRPD plot is consistent with that shown in FIG. 1.

XRPD patterns were collected with a PANalytical X'Pert PRO MPD diffractometer using an incident beam of Cu radiation produced using an Optix long, fine-focus source. An elliptically graded multilayer mirror was used to focus Cu Kα X-rays through the specimen and onto the detector. Prior to the analysis, a silicon specimen (NIST SRM 640c) was analyzed to verify the Si 111 peak position. A specimen of the sample was sandwiched between 3 μm-thick films and analyzed in transmission geometry. A beam-stop was used to minimize the background generated by air. Soller slits for the incident and diffracted beams were used to minimize broadening from axial divergence. Diffraction patterns were collected using a scanning position-sensitive detector (X'Celerator) located 240 mm from the specimen and Data Collector software v. 2.2b. The data-acquisition parameters were: X-ray Tube: Cu(1.546060 Å); Voltage: 45 kV, Amperage: 40 mA, Scan Range: 1.01-39.98°2θ; Step Size: 0.017°2θ; Collection Time 720 seconds; Scan Speed: 3.2°/min; Slit DS: ½°; Revolution Time: 1.0 second; Mode: transmission.

Scanning electron microscopy was also used to characterize the salt of this example. The results are shown in FIG. 7A-F (magnification from 50× to 10,000×). The crystalline structure of the salt is clearly evident. SEM was performed using a FEI Quanta 200 scanning electron microscope equipped with an Everhart Thornley (ET) detector. Images were collected and analyzed using xTm (v. 2.01) and XT Docu (v. 3.2) software, respectively. The magnification was verified using a NIST traceable standard. Each sample was prepared for analysis by placing a small amount on a carbon adhesive tab supported on an aluminum mount. Each sample was then sputter coated twice with Au/Pd using a Cressington 108auto Sputter Coater at approximately 20 mA and 0.13 mbar (Ar) for 75 seconds. The data acquisition parameters are displayed in the information bar at the bottom of each image. The magnification reported on each image was calculated upon the initial data acquisition.

It is noted that n-proponol can be substituted for ethanol in this example with identical results.

Example 33

Hemisuccinate Monohydrate of Compound 1

A slurry of 10 grams of Free base was charged to a reactor with 7 grams of water and 143 grams of ethanol and heated to 60° C. Separately, 2.5 grams of succinic acid and 36 grams of water were warmed to dissolve the succinic acid. One-fourth of the aqueous succinic acid was added to the free base mixture, which was heated to about 75° C. At 75° C., the remainder of the aqueous succinic acid solution was added over a 1 hour period. The batch was then cooled to 0° C. with two sets of heating/cooling cycles to enhance crystallinity. At 1° C., 143 ml of acetonitrile were added. The crystals were filtered and washed with aqueous acetonitrile and dried overnight at 30° C. under vacuum. The yield was 89.8% 11.6 grams. The actual water content was 5.5%

Example 34

Hemifumarate Monohydrate of Compound 1

A slurry of 10 grams of Free base was charged to a reactor with 7 grams of water and 73 grams of ethanol and heated to 40° C. Separately, 2.5 grams of succinic acid and 73 grams of ethanol were warmed to dissolve the fumaric acid. The fumaric acid solution was added to the free base solution and followed by the addition of 36 grams of water. The mixture was heated to about 80° C. The batch was then cooled to 1° C. with two sets of heating/cooling cycles to enhance crystallinity. At 1° C., 143 ml of acetonitrile were added. The crystals were filtered and washed with aqueous acetonitrile and dried overnight at 30° C. without vacuum. The yield was 82.9% 10.68 grams. The actual water content was 0.3%. The solids were exposed to high humidity to enable water content to rise to 4.6%.

Example 35

Hemi-L-Malate Monohydrate of Compound 1

A slurry of 10 grams of Free base was charged to a reactor with 7 grams of water and 143 grams of ethanol and heated to 60° C. Separately, 2.8 grams of L-malic acid and 36 grams of water were warmed to dissolve the L-malic acid. One-fourth of the aqueous L-malic acid was added to the free base mixture, which was heated to about 75° C. At 75° C., the remainder of the aqueous L-malic acid solution was added over a 1 hour period. The batch was then cooled to 0° C. with two sets of heating/cooling cycles to enhance crystallinity. At 0° C., 143 ml of acetonitrile were added. The crystals were filtered and washed with aqueous acetonitrile and dried overnight at 30° C. under vacuum. The yield was 81.8% 10.82 grams. The actual water content was 2.3%. The solids were exposed to high humidity to enable water content to rise to 4.9%.

Example 36

Hemi(Hemisuccinate, Hemifumarate) Monohydrate of Compound 1

A slurry of 10 grams of Free base was charged to a reactor with 7 grams of water and 70 grams of ethanol and heated to 45° C. Separately, 1.13 grams of fumaric acid and 1.15 grams of succinic acid were dissolved in 73 grams of warm ethanol and 36 grams of warm water, respectively. The acid solutions were added to the free base solution simultaneously and heated to about 61° C. The batch was then cooled to 0° C. with a set of heating/cooling cycles to enhance crystallinity. At 0° C., 143 ml of acetonitrile were added. The crystals were filtered and washed with aqueous acetonitrile and dried overnight at 30° C. under vacuum. The yield was 93.3% 12.04 grams. The actual water content was 5.7%.

Example 37

Hemi(Hemisuccinate, Hemi-L-Malate) Monohydrate of Compound 1

A slurry of 10 grams of Free base was charged to a reactor with 7 grams of water and 143 grams of ethanol and heated to 40° C. Separately, 1.31 grams of L-malic acid and 1.15 grams of succinic acid were dissolved in 36 grams of warm water. The acid solutions were added to the free base solution simultaneously and heated to about 61° C. The batch was then cooled to 0° C. with a set of heating/cooling cycles to enhance crystallinity. At 1-2° C., 143 ml of acetonitrile were added. The crystals were filtered and washed with aqueous acetonitrile and dried overnight at 30° C. under vacuum. The yield was 89.8% 11.75 grams. The actual water content was 1.1%. The solids were exposed to high humidity to enable the water content to rise to 5.3%.

Example 38

Hemi(Hemifumarate, Hemi-L-Malate) Monohydrate of Compound 1

A slurry of 10 grams of Free base was charged to a reactor with 7 grams of water and 70 grams of ethanol and heated to 40° C. Separately, 1.13 grams of fumaric acid and 1.31 grams of L-malic acid were dissolved in 73 grams of ethanol and 36 grams of warm water, respectively. The acid solutions were added to the free base solution simultaneously and heated to about 60° C. The batch was then cooled to 0° C. with a set of heating/cooling cycles to enhance crystallinity. At 0° C., 143 ml of acetonitrile were added. The crystals were filtered and washed with aqueous acetonitrile and dried overnight at room temperature under vacuum. The yield was 89.3% 12.04 grams. The actual water content was 2.8%. The solids were exposed to high humidity to enable the water content to rise to 5.3%.

Example 39

Hemi(⅓-Succinate, ⅓-Malate, ⅓-Fumarate) Monohydrate of Compound 1

A slurry of 10 grams of Free base was charged to a reactor with 7 grams of water and 70 grams of ethanol and heated to 42° C. Separately, 0.871 grams of L-malic acid and 0.767 grams of succinic acid were dissolved in 36 grams of warm water and 0.754 grams of fumaric acid were dissolved in 73 grams of warm ethanol. The acid solutions were added to the free base solution simultaneously and heated to about 70° C. The batch was then cooled to 0° C. with a set of heating/cooling cycles to enhance crystallinity. At 0° C., 143 ml of acetonitrile were added over a 1 hour period. The crystals were filtered and washed with aqueous acetonitrile and dried overnight at 50° C. under vacuum. The yield was 85.4% 11.1 grams. The actual water content was 3.2%. The solids were exposed to high humidity to enable the water content to rise to 5.2%.

Figure 8:
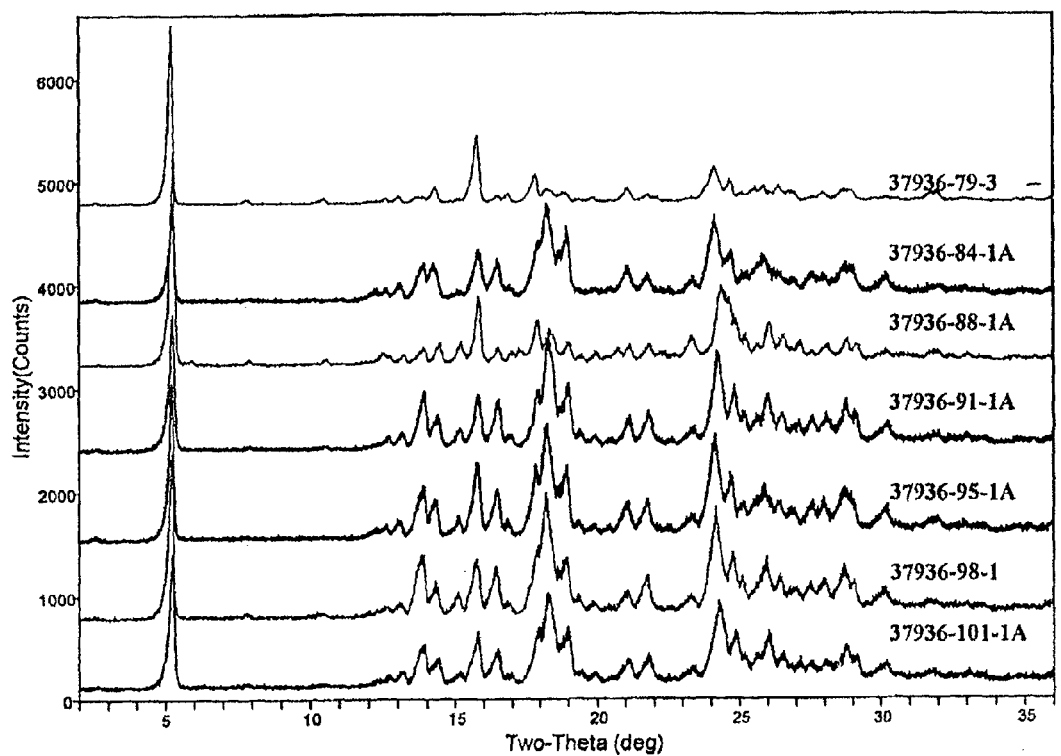
FIG. 8 the XRPD plots of the hemi(hemifumerate, hemi-L-malate), hemi(hemisuccinate, hemifumerate), hemi (hemisuccinate, hemi-L-malate), hemi(⅓-succinate, ⅓ fumarate, ⅓ L-malate), hemifumerate, hemi-L-malate and hemisuccinate salt forms of compound 1

XRPD analysis of the salts of Examples 33-39 were carried out and the results shown in FIG. 8. In FIG. 8, identity of the salt forms is, from bottom to top: hemi(hemifumarate, hemi-L-malate), 37936-101-1A; hemi(hemisuccinate, hemifumerate), 37936-98-1; hemi(hemisuccinate, hemi-L-malate), 37936-95-1A; hemi(⅓-succinate, ⅓ fumarate, ⅓ L-malate), 37936-91-1A; hemifumerate, 37936-88-1A; hemi-L-malate; 37936-84-1A; and hemisuccinate, 37936-79-3.

The salts of Examples 33-39 were also analyzed for water solubility at 25° C. in 50% aqueous ethanol (w/w %). The results are shown in Table 3. The solubility varied for the 7 salt forms from 2.6% hemi(⅓-succinate, ⅓ fumarate, ⅓-L-malate) monohydrate to 5.8% (hemi-L-malate monohydrate).

Table 4 provides a summary of other solid state data collected for the monohydrate salts of compound 1 described in Examples 33-39. The temperature at which the salts dehydrated per DSC is shown in column 2. The percent weight loss as determined by TGA is shown in column 3; the weight loss approximated theoretical weight loss. The result of exposure to humidity in a water sorption/desorption chamber shows that the original water content is recovered at high humidity as determined by dynamic vapor sorption (columns 4 and 5).

TABLE 1

Properties of Salts of Compound 1

| Salt | XRPD | DSC (Max ° C.) | TGA (% 150° C.) |
|---|---|---|---|
| Free Base | Partially Crystalline | 245 | 3.39 |
| Phosphate | Amorphous | n/a | n/a |
| Citrate | Crystalline | 158 | 2.74 |
| L-Tartrate | Partially Crystalline | 216 | 5.24 |
| Maleate | Crystalline | 169 | 2.80 |
| L-Lactate | Crystalline | 59, 103 | 5.36 |
| Stearate | Crystalline | 60, 164 | 1.82 |
| HBr | Highly crystalline | 235 | 0.73 |
| Tosylate | Highly crystalline | 202 | 0.71 |
| Acetate | Crystalline | 90, 119 | 20.82 |
| Hemisulfate | Crystalline | 234 | 3.48 |
| Monofumarate | Crystalline | 228 | 2.71 |
| Monosuccinate | Crystalline | 78, 195 | 0.62 |
| L-Malate | Crystalline | 80, 201 | 4.52 |

TABLE 2

Properties of Selected $C_4$ Dicarboxylic Acid Salts of Compound 1

| Acid | Salt Form | XRPD (characteristic peaks) | DSC (Max ° C.) | TGA (% 150° C.) |
|---|---|---|---|---|
| Succinic | Hemisuccinate Monohydrate | 5.4, 14.0, 14.5, 16.0, 16.6, 18.0, 18.4, 19.1, 22.0, 24.3, 24.9 | 76, 211 | 5.37 |
| | Hemisuccinate Anhydrate I | 5.7, 11.6, 12.8, 15.5, 16.1, 16.8, 17.4, 20.7, 22.3, 23.5, 24.4 | 220 | 0.22 |
| | Hemisuccinate Anhydrate II | 5.5, 12.8, 13.3, 14.1, 14.5, 15.5, 16.7, 18.5, 19.3, 19.7, 24.4 | 178, 209 | 0.17 |
| Fumaric | Hemifumarate Monohydrate | 5.3, 13.9, 14.5, 15.9, 16.6, 18.0, 18.4, 19.1, 21.9, 24.4, 25.0 | 70, 220 | 5.56 |
| | Hemifumarate Anhydrate I | 5.9, 9.3, 12.5, 15.2, 17.3, 17.8, 20.8, 22.4, 23.4, 24.7, 25.3 | 240 | 0.26 |
| | Hemifumarate Anhydrate II | 5.7, 13.1, 15.1, 17.3, 18.6, 22.6, 23.7, 24.4, 24.8 | 217 | 0.50 |
| Malic | Hemimalate Monohydrate | 5.4, 14.1, 14.5, 16.0, 16.6, 18.0, 18.4, 19.1, 22.0, 24.4, 24.9 | 80, 201 | 4.52 |
| Succinic/ Fumaric | Hemi(hemisuccinate-hemifumarate) monohydrate | 5.3, 14.0, 14.5, 15.9, 16.6, 17.9, 18.4, 19.1, 21.2, 24.3, 24.9 | 76, 208 | 5.71 |
| Succinic/ Malic | Hemi(hemisuccinate-hemimalate) monohydrate | 5.3, 13.2, 14.5, 15.9, 17.0, 18.0, 18.6, 19.0, 21.3, 24.3, 24.9 | 86, 200 | 4.68 |

TABLE 2-continued

Properties of Selected C$_4$ Dicarboxylic Acid Salts of Compound 1

| Acid | Salt Form | XRPD (characteristic peaks) | DSC (Max ° C.) | TGA (% 150° C.) |
|---|---|---|---|---|
| Fumaric/ Malic | Hemi(hemifumarate-hemimalate) monohydrate | 5.3, 14.0, 14.5, 15.9, 16.6, 18.0, 18.4, 19.1, 21.2, 24.4, 25.0 | 81, 208 | 5.32 |

TABLE 3

Solubility in 50% Ethanol

| Monohydrate Salt of Compound 1 | Wt % solubility at 25° C. |
|---|---|
| Hemisuccinate | 2.8% |
| Hemifumarate | 3.0% |
| Hemi-L-malate | 5.8% |
| Hemi(hemisuccinate, hemifumarate) | 3.0% |
| Hemi(hemisuccinate, hemi-L-malate) | 3.7% |
| Hemi(hemifumarate, hemi-L-malate) | 3.5% |
| Hemi(⅓-succinate, 1.3-fumarate, ⅓-L-malate) | 2.6% |

TABLE 4

Summary of Solid State Data

| Salt of Compound 1 | Dehydration Temp (° C.) from DSC | Weight loss by 125° C. from TGA | Weight gain from 0 to 20% RH from DVS | Weight gain from 0 to 90% RH from DVS |
|---|---|---|---|---|
| Hemisuccinate | 79 | 5.4 | 5.44 | 6.04 |
| Hemi-L-malate | 66 | 4.8 | 0.87 | 5.68 |
| Hemifumarate | 80 | 4.4 | 4.07 | 5.31 |
| Hemi(⅓-succinate, ⅓-fumarate, ⅓-L-malate | 78 | 5.2 | 4.36 | 5.95 |
| Hemi(hemisuccinate, hemi-L-malate) | 72 | 5.3 | 4.41 | 5.12 |
| Hemi(hemisuccinate, hemifumerate) | 67 | 5.5 | 5.11 | 6.11 |
| Hemi(hemi-L-malate, hemifumerate) | 71 | 5.0 | 4.05 | 5.81 |

What is claimed is:

1. A salt of compound 1:

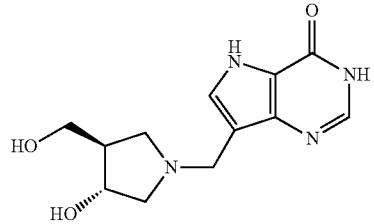

wherein the salt of compound 1 is a hemi salt with a C$_4$ organic diacid, the C4 organic diacid being selected from the group consisting of succinic, fumaric, L-malic or a mixture thereof wherein the salt exhibits no polymorphic variants or a reduced number of polymorphic variants.

2. The salt according to claim 1, wherein the C$_4$ organic diacid is selected from the group consisting of succinic, fumaric, and L-malic acids.

3. The salt according to claim 1, wherein the salt is a mixed salt.

4. The salt according to claim 3, wherein the salt is selected from the group consisting of hemi(hemisuccinate, hemifumarate) monohydrate, hemi(hemisuccinate, hemimalate) monohydrate, and hemi(hemifumarate, hemimalate) monohydrate.

5. The salt according to claim 1, wherein the salt is the hemisuccinate monohydrate.

\* \* \* \* \*